US007816484B2

(12) United States Patent
Verral

(10) Patent No.: US 7,816,484 B2
(45) Date of Patent: Oct. 19, 2010

(54) METHOD FOR MAKING POLYETHYLENE GLYCOL CARBONATES

(75) Inventor: Daniel E. Verral, Midland, MI (US)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 12/280,849

(22) PCT Filed: Feb. 27, 2007

(86) PCT No.: PCT/US2007/005094

§ 371 (c)(1),
(2), (4) Date: Oct. 24, 2008

(87) PCT Pub. No.: WO2007/100829

PCT Pub. Date: Sep. 7, 2007

(65) Prior Publication Data

US 2009/0054621 A1 Feb. 26, 2009

Related U.S. Application Data

(60) Provisional application No. 60/777,374, filed on Feb. 28, 2006.

(51) Int. Cl.
*C08G 63/00* (2006.01)
*C08G 63/02* (2006.01)
(52) U.S. Cl. ........................ 528/271; 528/198; 528/272; 549/512; 549/514
(58) Field of Classification Search ................ 528/271, 528/272, 198; 549/512, 514
See application file for complete search history.

(56) References Cited

U.S. PATENT DOCUMENTS

| 5,286,637 A | 2/1994 | Veronese et al. |
| 5,366,735 A | 11/1994 | Henry |
| 5,919,455 A | 7/1999 | Greenwald et al. |
| 5,932,462 A | 8/1999 | Harris et al. |
| 6,280,745 B1 | 8/2001 | Flore et al. |
| 2003/0065134 A1 | 4/2003 | Sakanoue et al. |

FOREIGN PATENT DOCUMENTS

WO 97/32607 A2 9/1997

OTHER PUBLICATIONS

S. Zalipsky, "Functionalized Poly(ethylene glycol) for Preparation of Biologically Relevant Conjugates", Bioconjugate Chem., vol. 6, pp. 150-165, 1995.
Henmanson, "Modification with Synthetic Polymers", Bioconjugate Techniques, Chapter 15, 1996.
J. E. Seely, et al., "Use of Ion-Exchange Chromatography and Hydrophobic Interaction Chromatography in the Preparation and Recovery of Polyethylene Glycol-Linked Proteins", Journal of Chromatography A., vol. 908, pp. 235-241, 2001.
G. Fortier, et al., "Surface Modification of Horseradish Peroxidase with Poly(Ethylene Glycols)s of Various Molecular Masses", Biotechnology Applied Biochemistry, vol. 17, pp. 115-130, 1993.
F. M. Veronese, et al., "Surface Modification of Proteins-Activation of Monomethoxy-Polyethylene Glycols by Phenylchloroformates and Modification of Ribonuclease and Superoxide Dismutase", Applied Bochem. Biotech., vol. 11, pp. 141-152, 1985.

*Primary Examiner*—Terressa M Boykin
(74) *Attorney, Agent, or Firm*—Balaram Gupta; Thomas C. McKenzie; Robert A. Franks

(57) ABSTRACT

A method for preparing a polyalkylene glycol carbonate is disclosed comprising reacting a hydroxyl functional polyalkylene glycol and a reagent selected from carbonates and chloroformates in the presence of an aromatic solvent and an amine.

13 Claims, No Drawings

METHOD FOR MAKING POLYETHYLENE GLYCOL CARBONATES

FIELD OF THE INVENTION

This invention is in the field of methods for making polyethylene glycol carbonates.

BACKGROUND OF THE INVENTION

Biologically active compounds conjugated with polyoxyalkylenes (such as polyethylene glycol) can provide enhanced biocompatibility for the compound. See, for example, U.S. Pat. Nos. 5,366,735 and 6,280,745. A review of this subject by Zalipsky, in Bioconjugate Chem., 1995, 6, p150-165, identified polyethylene glycol as one of the best biocompatible polymers to conjugate with a biologically active compound (such as a drug, a protein, a peptide or an enzyme) to produce a conjugate having improved properties such as compatible solubility characteristics, reduced toxicity, improved surface compatibility, increased circulation time and reduced immunogenicity.

Polyethylene glycol (PEG) is a linear polyoxyalkylene terminated at the ends thereof with hydroxyl groups and generally represented by the formula: $HO(CH_2CH_2O)_nH$. As discussed by Henmanson in Chapter 15 of Bioconjugate Techniques (1996), monomethyl polyethylene glycol (mPEG) generally represented by the formula: $CH_3O(CH_2CH_2O)_nH$, is often used to prepare a polyethylene glycol conjugate with a biologically active compound typically by way of a coupling reaction between the biologically active compound and a derivative of MPEG such as mPEG p-nitrophenyl carbonate. A biologically active compound coupled to PEG is said in the art to be "PEGylated".

As discussed by Seely and Richey, J. of Chrom. A, 908 (2001) 235-241 herein fully incorporated by reference, the serum half-life of a PEGylated biopharmaceutical agent increases as the molecular weight of the PEG chain is increased. One means of increasing the molecular weight of a PEG derivatizing agent is to form a "multi-armed" PEG derivative. A multi-armed PEG derivative comprises a plurality of PEG chains thereby increasing the molecular weight of the multi-armed PEG derivative. A multi-armed PEG derivative can be multi-functional (as discussed by Seely and Richey, by WO 97/32607 and by USPAP 2003/0065134 each of which are herein fully incorporated by reference) or mono-functional (as discussed by U.S. Pat. Nos. 5,919,455 and 5,932,462 each of which are herein fully incorporated by reference).

The prior art methods for making mPEG carbonates, such as mPEG p-nitrophenyl carbonate, are set forth in U.S. Pat. No. 5,286,637, by Fortier et al. Applied Biochemistry (1993) 17(1), 115-130 and by Veronese et al., Applied Biochem. Biotech. 11, 141-152 (1985). U.S. Pat. No. 5,286,637 is based on the reaction of mPEG with p-nitrophenyl chloroformate in a solvent of methylene chloride containing triethylamine. Fortier et al. used pyridine instead of triethylamine. Veronese et al. used acetonitrile instead of methylene chloride. All of these prior art methods for making MPEG p-nitrophenyl carbonate also produce an impurity (believed to be the amine salt of the hydrolyzed MPEG p-nitrophenyl carbonate) when the concentration of the MPEG p-nitrophenyl carbonate is relatively high, which impurity is difficult to separate from the mPEG p-nitrophenyl carbonate. Thus, there remains a need for an improved method for making mPEG carbonates (such as MPEG p-nitrophenyl carbonate) at relatively high concentration, which method never-the-less produces less impurity.

SUMMARY OF THE INVENTION

The instant invention is a method for making polyalkylene glycol carbonates, preferably polyethylene glycol carbonates, which produces less of the above-mentioned type of impurity. More specifically, the instant invention is a method comprising reacting a polyalkylene glycol (preferably PEG) comprising at least one hydroxyl group with a reagent selected from carbonates and chloroformates in the presence of an aromatic solvent and an amine. According to one preferred embodiment, this is a method for making a linear, preferably alkyl terminated) polyalkylene glycol carbonate (preferably an alkyl polyethylene glycol carbonate) comprising the step of reacting mono-alkyl polyalkylene glycol (preferably mono-alkyl PEG) with a reagent selected from carbonates and chloroformates in the presence of an aromatic solvent and an amine. In a related embodiment, the instant invention is a method for making a multi-armed polyalkylene glycol carbonate (preferably multi-armed PEG carbonate) comprising the step of reacting a multi-armed polyalkylene glycol (preferably multi-armed PEG) having at least one hydroxyl group with a reagent selected from carbonates and chloroformates in the presence of an aromatic solvent and an amine.

DETAILED DESCRIPTION

Preferably, the amine used in this invention has the formula $R_3N$, wherein R is independently in each occurrence an organic group comprising two or more carbon atoms. R may be a hydrocarbon containing only carbon and hydrogen or alternatively may be a moiety containing heteroatoms. The groups R can comprise linear, branched, saturated or unsaturated cyclic or polycyclic structure. Preferably, R is an aliphatic or aromatic hydrocarbon with alkyls being most preferred. R, preferably, comprises independently in each occurrence less than ten carbon atoms. A highly preferred amine is tripentylamine.

The reagent may be any carbonate or chloroformate reagent which would react with the hydroxyl group on the polyalkylene glycol to form a carbonate group. Preferably, a chloroformate is used. The chloroformate is preferably an aryl chloroformate, more preferably a phenyl chloroformate, and most preferably is p-nitrophenyl chloroformate.

The term "aromatic solvent" means a solvent comprising unsaturated cyclic groups containing one or more rings. A highly preferred aromatic solvent is toluene.

According to the preferred embodiment where the polyalkylene glycol is linear and alkyl terminated the compound may be represented by the formula:

$R^1$—(O—$R^2$)—OH where $R^1$ is a hydrocarbon group, preferably an alkyl group of more preferably at least 1 carbon atom and more preferably no more than 7 carbon atoms, more preferably still 1 or 2 carbon atoms and $R^2$ is a hydrocarbon, preferably an alkylene group of more preferably at least 1 carbon atom and more preferably no more than 5 carbon atoms. $R^1$ is most preferably methyl and $R^2$ is most preferably ethylene.

According to the alternate embodiment the polyalkylene glycol (PAG) is "multi-armed". As used herein a multiarmed polyalkylene glycol has a common core and one or more hydroxyl groups on the end of a PAG chain or at a point or points other than at the end of the PAG chain provided that if the PAG is linear, the PAG chain has at least two hydroxyl groups. Preferably the polyalkylene glycol is a multi-armed polyethylene glycol carbonate which can be mono-functional (comprising one carbonate group) or poly-functional (comprising more than one carbonate group).

Optionally, the mono-alkyl polyethylene glycol and the aromatic solvent can be mixed and dried by azeotropic distillation before adding the chloroformate and the amine. Preferably, the reaction is conducted at a temperature in the range of from 25 to 75 degrees Celsius. Most preferably, the reaction is conducted at a temperature in the range of from 50 to 60 degrees Celsius and the chloroformate is p-nitrophenyl chloroformate. The mole ratio of chloroformate to polyalkylene glycol is preferably at least 5:1, more preferably at least 8:1 and preferably no more than 20:1, more preferably no more than 12:1. The mole ratio of the amine to mono-alkyl polyethylene glycol is preferably at least 2.5:1, more preferably at least 4:1 and preferably no more than 10:1, more preferably no more than 6:1. The amount of solvent used per kilogram of mono-alkyl polyethylene glycol is preferably at least 2 liters more preferably at least 4 liters, and preferably no more than 10 liters, more preferably no more than 6 liters.

The polyalkylene glycol preferably has a number average molecular weight of at least about 500, more preferably at least about 1000, and most preferably at least about 5000. The number average molecular weight is preferably no greater than about 100,000, more preferably no greater than about 60,000.

The linear alkyl polyalkylene glycol carbonate compositions of the instant invention are preferably characterized by low polydispersity and relatively high defined molecular weight each as determined by size exclusion chromatography. Low polydispersity means polydispersity of less than 1.1. The alkyl polyethylene glycol carbonate preferably has a number average molecular weight of at least about 500, more preferably at least about 1000, and most preferably at least about 5000. The number average molecular weight is preferably no greater than about 100,000, more preferably no greater than about 60,000. The specific molecular weight may be chosen to suit the particular biomedical application for which the composition is required, for example a molecular weight of 10,000, 20,000, 30,000 or 40,000.

The polyalkylene glycol carbonate (for convenience, the preferred methylPEG carbonate or mPEG carbonate will be referred to throughout this process description section but should not be considered as limiting) is preferably isolated by cooling the mixture and adding an anti-solvent (such as an ether, e.g. MTBE, or an alkane, e.g. hexane or heptane) to precipitate the product, filtering the precipitate, and washing it with fresh anti-solvent. The MPEG carbonate is then preferably purified by redissolving in a solvent (such as methanol or THF), adding an anti-solvent (such as isopropanol, and ether, e.g. MTBE, or an alkane, e.g. hexane or heptane) to precipitate the product, filtering the precipitate, and washing it with fresh anti-solvent. The mPEG carbonate can then be dried in a vacuum oven at 25-35 degrees Celsius. The product is preferably analyzed by proton NMR and liquid chromatography under critical conditions.

EXAMPLE 1

To a 20 L straight-walled jacketed reactor with bottom drain and thermowell, equipped with an overhead stirrer, cold water condenser and nitrogen inlet, is charged one kilogram of 20,000 gram per mole average molecular weight mPEG having a polydispersity of less than 1.1 and six liters of toluene. The resulting solution stirred (250 rpm) while heating to 60° C. before adding 73 milliliters of tripentylamine and 101 grams of p-Nitrophenylchloroformate. An immediate yellow color forms, but quickly dissipates. The reaction is allowed to stir at 60° C. under an inert atmosphere until HPLC analysis under critical conditions indicates an essentially complete reaction. After approximately 18-24 hours of heating, the reaction is cooled to 35° C. and methyl t-butyl ether (MTBE; 10 L; 10 mL per gram mPEG-OH) is added all at once with increased agitation (350 rpm). The resulting thick slurry is cooled to 0° C. and stirred 30 minutes before isolating the solid on a sintered glass funnel by vacuum filtration. The reaction flask is rinsed with ice cold MTBE (2.0 L; 2 mL per gram mPEG-OH) and this rinse used to wash the isolated solid. The solid is left under aspirator vacuum until no additional filtrate is evident. The semi-dry solid is then transferred back to the 20 L reactor and methanol (MeOH; 2.2 L; 2.2 mL per gram mPEG-OH) is added, including a 100 mL MEOH rinse on the isolation funnel. The resulting mixture is stirred gently (200 rpm) while heating to 40° C. under an inert atmosphere until a homogeneous solution is obtained (NOTE: if the solution remains hazy, it is preferably filtered again). Isopropanol (IPA; 13.8 L; 13.8 mL per gram MPEG-OH) is added over 1 hour and the solids start to precipitate out of solution. The mixture is then cooled to 0° C. The resulting thick slurry is stirred for 60 minutes before isolating the solid on a sintered glass funnel by vacuum filtration. The reaction flask is rinsed with cold IPA (6.3 L; 6.3 mL per gram mPEG-OH) and this rinse is used to wash the isolated solid. The solid is left under aspirator vacuum until no additional filtrate is evident. The semi-dry solid is dissolved in MeOH and re-precipitated from MeOH/IPA as described above two additional times. The final wet-cake is dried under high vacuum at 40° C. for 48 hours to give approximately 850 g of product as a white to light yellow solid. The product is analyzed by high performance liquid chromatography under critical conditions and by proton NMR.

EXAMPLE 2

To a 20 L straight-walled jacketed reactor with bottom drain and thermowell, equipped with an overhead stirrer, cold water condenser and nitrogen inlet, is charged 700 grams of 10,000 gram per mole average molecular weight mPEG having a polydispersity of less than 1.1 and four liters of toluene. The resulting solution stirred (250 rpm) while heating to 60° C. before adding 100 milliliters of tripentylamine and 140 grams of p-Nitrophenylchloroformate. An immediate yellow color forms, but quickly dissipates. The reaction is allowed to stir at 60° C. under an inert atmosphere until HPLC analysis under critical conditions indicates an essentially complete reaction. After approximately 18-24 hours of heating, the reaction is cooled to 35° C. and methyl t-butyl ether (MTBE; 7 L; 10 mL per gram mPEG-OH) is added all at once with increased agitation (350 rpm). The resulting thick slurry is cooled to 0° C. and stirred 30 minutes before isolating the solid on a sintered glass funnel by vacuum filtration. The reaction flask is rinsed with ice cold MTBE (1.4 L; 2 mL per gram mPEG-OH) and this rinse used to wash the isolated solid. The solid is left under aspirator vacuum until no additional filtrate is evident. The semi-dry solid is then transferred back to the 20 L reactor and methanol (MeOH; 1.4 L; 2.2 mL per gram mPEG-OH) is added, including a 100 mL MeOH rinse on the isolation funnel. The resulting mixture is stirred gently (200 rpm) while heating to 40° C. under an inert atmosphere until a homogeneous solution is obtained (NOTE: if the solution remains hazy, it is preferably filtered again). Isopropanol (IPA; 9.6 L; 13.8 mL per gram mPEG-OH) is added over 1 hour and the solids start to precipitate out of solution. The mixture is then cooled to 0° C. The resulting thick slurry is stirred for 60 minutes before isolating the solid on a sintered glass funnel by vacuum filtration. The reaction flask is rinsed with cold IPA (4.4 L; 6.3 mL per gram MPEG-OH) and this rinse is used to wash the isolated solid. The solid is left under aspirator vacuum until no additional filtrate is evident. The semi-dry solid is dissolved in MeOH and re-precipitated from MeOH/IPA as described above two additional times. The final wet-cake is dried under high vacuum at 40° C. for 48 hours to give approximately 666 grams of product as a white to light yellow solid. The product is analyzed by high performance liquid chromatography under critical conditions and by proton NMR.

Critical Condition Liquid Chromatography Conditions

A high pressure liquid chromatograph instrument is equipped with an evaporative light scattering detector and a UV detector set at 270 nm. The column is a Zorbax 330 SB (4/6×150 mm, 5 micron pore size) and is kept at 29 degrees Celsius. The eluants are (A) 40/60 v/v acetonitrile water, and (B) 50/50 v/v acetonitrile/water.

Suitable equipment to use includes Agilent 1100 Series Liquid Chromatograph: Quaternary Pump G1311A; Vacuum Degasser G1322A; Autosampler G1313A ALS; Column Thermostat G1313A COLCOM; Variable Wavelength Detector G1314A.Alltech 2000 Evaporative Light Scattering Detector.

Zorbax 300SB-C18 4.6×150 mm, 5 micron column at 29 degrees Celsius 0.75 mL/min Eluant Flow Rate.

5 microliter Injection Volume.

UV detection at 270 nanometers, peak width greater than 0.1 minute, response time 2 seconds, attenuation 1000 mAu.

Evaporative Light Scattering Detector: gas flow 3.0 mL/min N2, tube temp 110° C., Gain 1, Impactor Off.

Software: Agilent LC Chemstation Revision A.09.01.

Eluant: (A) 40/60 v/v acetonitrile/water; (B) 50/50 v/v acetonitrile/water.

Critical condition is determined by combining eluents (A) and (B) in a ratio so that PEG diols with molecular weights of 6K and 36K have the same retention time.

Sample Preparation: Dry PEG samples are dissolved at 50 mg/1 gram of eluent A. Wet cakes of PEG in MTBE are dissolved at 80 mg/1 gram of eluent A. Wet cakes of PEG in IPA are dissolved at 150 mg/1 gram of eluent A.

CONCLUSION

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

What is claimed is:

1. A method for making a polyalkylene glycol carbonate comprising the step of reacting a hydroxyl functional polyalkylene glycol and a reagent that is an aryl chloroformate in the presence of an aromatic solvent and an amine.

2. The method of claim 1 where the polyalkylene glycol carbonate is linear and terminates in an alkyl group at one end and a carbonate at the other end.

3. The method of claim 1 where the polyalkylene glycol is methyl polyethylene glycol.

4. The method of claim 1 wherein the polyalkylene glycol carbonate is multi-armed.

5. The method of claim 1 where the polyalkylene glycol is polyethylene glycol.

6. The method of claim 1 where the reagent is p-nitrophenyl chloroformate.

7. The method of claim 1 wherein the amine has the formula $R_3N$, wherein R is independently in each occurrence an organic group comprising two or more carbon atoms.

8. The method of claim 7 where R is an alkyl group.

9. The method of claim 1 wherein the reaction is conducted at a temperature in the range of from 25 to 75° Celsius.

10. The method of claim 6, wherein the mole ratio of p-nitrophenyl chloroformate to polyalkylene glycol is in the range of from 5:1 to 20:1.

11. The method of claim 1 wherein from 2 to 10 liters of aromatic solvent are used per kilogram of polyalkylene glycol.

12. The method of claim 1, wherein the aromatic solvent is toluene, and the amine is tripentylamine.

13. The method of claim 1, wherein the mole ratio of the reagent to the polyalkylene glycol is in the range of from 8:1 to 12:1, the mole ratio of the amine to the polyalkylene glycol is in the range of from 4:1 to 6:1 and from 4 to 6 liters of toluene are used per kilogram of polyalkylene glycol.

* * * * *